US009884827B2

(12) United States Patent
Afzali-Ardakani et al.

(10) Patent No.: US 9,884,827 B2
(45) Date of Patent: Feb. 6, 2018

(54) SELECTIVE PLACEMENT OF CARBON NANOTUBES VIA COULOMBIC ATTRACTION OF OPPOSITELY CHARGED CARBON NANOTUBES AND SELF-ASSEMBLED MONOLAYERS

(71) Applicant: International Business Machines Corporation, Armonk, NY (US)

(72) Inventors: Ali Afzali-Ardakani, Ossining, NY (US); Hongsik Park, Yorktown Heights, NY (US); George S. Tulevski, Croton-on-Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/001,802

(22) Filed: Jan. 20, 2016

(65) Prior Publication Data

US 2016/0137605 A1  May 19, 2016

Related U.S. Application Data

(63) Continuation of application No. 13/248,176, filed on Sep. 29, 2011, now Pat. No. 9,273,004.

(51) Int. Cl.
*H01L 29/06* (2006.01)
*C07D 213/79* (2006.01)
(Continued)

(52) U.S. Cl.
CPC .......... *C07D 213/79* (2013.01); *B82Y 10/00* (2013.01); *C07D 213/76* (2013.01);
(Continued)

(58) Field of Classification Search
USPC ................................. 438/99, 164, 98, 299
See application file for complete search history.

(56) References Cited

U.S. PATENT DOCUMENTS 5,301,143 A   4/1994  Ohri et al.
6,733,828 B2  5/2004  Chao et al.
(Continued)

FOREIGN PATENT DOCUMENTS

CN  101950685 A   1/2011
JP  2006522853 A  10/2006
(Continued)

OTHER PUBLICATIONS

European Search Report dated Mar. 13, 2015 for Application No. 12836212.6.
(Continued)

*Primary Examiner* — Moin Rahman
(74) *Attorney, Agent, or Firm* — Cantor Colburn LLP; Vazken Alexanian

(57) ABSTRACT

A method of forming a structure having selectively placed carbon nanotubes, a method of making charged carbon nanotubes, a bi-functional precursor, and a structure having a high density carbon nanotube layer with minimal bundling. Carbon nanotubes are selectively placed on a substrate having two regions. The first region has an isoelectric point exceeding the second region's isoelectric point. The substrate is immersed in a solution of a bi-functional precursor having anchoring and charged ends. The anchoring end bonds to the first region to form a self-assembled monolayer having a charged end. The substrate with charged monolayer is immersed in a solution of carbon nanotubes having an opposite charge to form a carbon nanotube layer
(Continued)

on the self-assembled monolayer. The charged carbon nanotubes are made by functionalization or coating with an ionic surfactant.

3 Claims, 9 Drawing Sheets

(51) Int. Cl.
*C07D 213/76* (2006.01)
*B82Y 10/00* (2011.01)
*B82Y 40/00* (2011.01)
*H01L 51/00* (2006.01)
*H01L 51/05* (2006.01)

(52) U.S. Cl.
CPC ...... *H01L 51/0048* (2013.01); *H01L 51/0049* (2013.01); *B82Y 40/00* (2013.01); *H01L 29/0676* (2013.01); *H01L 51/0003* (2013.01); *H01L 51/0558* (2013.01)

(56) References Cited

U.S. PATENT DOCUMENTS

| | | | |
|---|---|---|---|
| 6,900,479 | B2 | 5/2005 | DeHon et al. |
| 6,969,690 | B2 | 11/2005 | Zhou et al. |
| 7,312,100 | B2 | 12/2007 | Bocian et al. |
| 7,504,132 | B2 | 3/2009 | Afzali-Ardakani et al. |
| 7,517,587 | B2 | 4/2009 | Mioskowski et al. |
| 7,531,293 | B2 | 5/2009 | Afzali-Ardakani et al. |
| 7,680,306 | B2 | 3/2010 | Boutant et al. |
| 7,692,952 | B2 | 4/2010 | DeHon |
| 7,732,119 | B2 | 6/2010 | Afzali-Ardakani et al. |
| 7,759,063 | B2 | 7/2010 | Cha et al. |
| 7,855,133 | B2 | 12/2010 | Afzali-Ardakani et al. |
| 7,888,528 | B2 | 2/2011 | Afzali-Ardakani et al. |
| 7,891,567 | B2 | 2/2011 | Burden et al. |
| 8,028,924 | B2 | 10/2011 | Anderson et al. |
| 8,216,636 | B2 | 7/2012 | Chan et al. |
| 2003/0089899 | A1 | 5/2003 | Lieber et al. |
| 2003/0211129 | A1* | 11/2003 | Spillman, Jr. ......... A61L 27/303 424/423 |
| 2006/0041104 | A1* | 2/2006 | Ait-Haddou ........... B82Y 30/00 528/397 |
| 2006/0115640 | A1 | 6/2006 | Yodh et al. |
| 2006/0279191 | A1 | 12/2006 | Geohegan et al. |
| 2008/0102213 | A1 | 5/2008 | Afzali-Ardakani et al. |
| 2009/0117277 | A1 | 5/2009 | Afzali-Ardakani et al. |
| 2009/0170725 | A1 | 7/2009 | Yamakawa et al. |
| 2009/0232724 | A1 | 9/2009 | Afzali-Ardakani et al. |
| 2009/0301349 | A1 | 12/2009 | Afzali-Ardakani et al. |
| 2009/0320911 | A1 | 12/2009 | Ruoff |
| 2010/0003616 | A1* | 1/2010 | Afzali-Ardakani ... C07C 271/20 430/270.1 |
| 2010/0032197 | A1 | 2/2010 | Hong et al. |
| 2010/0044074 | A1 | 2/2010 | Kim et al. |
| 2010/0044678 | A1 | 2/2010 | Afzali-Ardakani et al. |
| 2010/0224354 | A1 | 9/2010 | Dooley et al. |
| 2010/0247381 | A1 | 9/2010 | Yodh et al. |
| 2010/0256344 | A1 | 10/2010 | Thompson et al. |
| 2011/0198542 | A1 | 8/2011 | Chung et al. |
| 2013/0082233 | A1 | 4/2013 | Afzali-Ardakani et al. |
| 2015/0317494 | A1 | 11/2015 | Lobez Comeras, et al. |
| 2016/0141501 | A1 | 5/2016 | Afzali-Ardakani et al. |

FOREIGN PATENT DOCUMENTS

| | | |
|---|---|---|
| JP | 2008258532 A | 10/2008 |
| WO | 0152207 A1 | 7/2001 |
| WO | 2005017953 A2 | 2/2005 |
| WO | 2008013508 A1 | 1/2008 |

OTHER PUBLICATIONS

Agboola, Bolade O., et al.; "Electrochemical Characterization of Mixed Self-Assembled Filsm of Water-Soluble Single-Walled Carbon Nanotube-Poly(m-aminobenzene sulfonic acid) and Iron(II) Tetrasulfophthalocyanine"; Journal of the Electrochemical Society.
C.Klinke et al., "Field-Effect Transistors Assembled from Functionalized Carbon Nanotubes", Nano Letters, 2006, vol. 6, No. 5, pp. 906-910.
E.J. Wallace et al, "Carbon nanotube self-assembly with lipids and detergent: a molecular dynamics study", Nanotechnology, vol. 20, 2009, 045102, 6 Pages.
F. Cheng et al, "Supramolecular Functionalization of Single-Walled Carbon Nanotubes with Conjugated Polyelectrolytes and Their Patterning on Surfaces", Macromolecules, 2008, vol. 41, pp. 9869-9874.
G.S. Tulevski et al, "Chemically Assisted Directed Assembly of Carbon Nanotubes for the Fabrication of Large-Scale Device Arrays", JACS (J.AM.CHEM.SOC.) Articles, 2007, vol. 129, pp. 11964-11968.
J. Liu et al., "Controlled Deposition of Individual Single-Walled Carbon Nanotubes on Chemically Functionalized Templates", Chemical Physics Letters 303, Apr. 2, 1999, pp. 125-129.
J.A. Bardecker et al., "Directed Assembly of Single-Walled Carbon Nanotubes via Drop-Casting onto a UV-Patterned Photosensitive Monolayer", J.Am. Chem. Soc., vol. 130, No. 23.2008, pp. 7226-7227.
J.B. Hannon et al., "Selective Placement of Carbon Nanotubes on Metal-Oxide Surfaces", Langmuir, 2005, vol. 21, No. 19, pp. 8569-8571.
J.P. Bourgoin et al., "Directed assembly for carbon nanotube device fabrication", 2006 International Electron Devices Meeting., IEDM '06., Dec. 11-13, 2006, 4 Pages.
Lee, Seung Woo, et al.; "Layer-by-Layer Assembly of All Carbon Nanotube Ultrathin Films for Electrochemical Applications"; J. Am. Chem. Soc.; vol. 131; p. 671-679; 2009.
Liu, Zhongfan, et al.; "Organizing Single-Walled Carbon Nanotubes on Gold Using a Wet Chemical Self-Assembling Technique"; Langmuir; vol. 16, No. 8; p. 3569-3573; 2000.
M.C. Hersam, "Progress towards monodisperse single-walled carbon nanotubes", Nature Nanotechnology, 2008, vol. 3, pp. 387-394.
Pengfei Wu, et al., "Backward Scattering Effect of Aligned Carbon Nanotube Arrays," Proceedings of SPIE, vol. 7223, Feb. 2009, 72231A, pp. 1-8.
S.G. Rao, "Nanotube Electronics: Large-Scale Assembly of Carbon Nanotubes", Brief Communications, Nature, Sep. 4, 2003, vol. 425, pp. 36-37.
T. Hertal et al., "Spectroscopy of Single-and Double-Wall Carbon Nanotubes in Different Environments", Nano Letters, 2005, vol. 5, No. 3, pp. 511-514.
Tetsu Yonezawa, et al.; "Preparation of Noble Metal Nanoparticles by Using of Cationic Isonitrile Ligands"; 50th The Society of Polymer Science, Japan,Proceeding; vol. 50, No. 3; p. 1-4; May 7, 2001.
Tulevski, George S., et al.; "Chemically Assisted Directed Assembly of Carbon Nanotubes for the Fabrication of Large-Scale Device Arrays"; J. Am. Chem. Soc.; vol. 129; p. 11964-11968; 2007.
Yoo, Bum Keun, et al.; "Self-Assembly of Functionalized Single-Walled Carbon Nanotubes Prepared from Aryl Diazonium Compounds of Ag Surfaces"; Materials Letters; vol. 60; p. 3224-3226; 2006.
List of IBM Patents or Patent Applications Treated as Related; (Appendix P), filed Sep. 15, 2017; 2 pages.

* cited by examiner

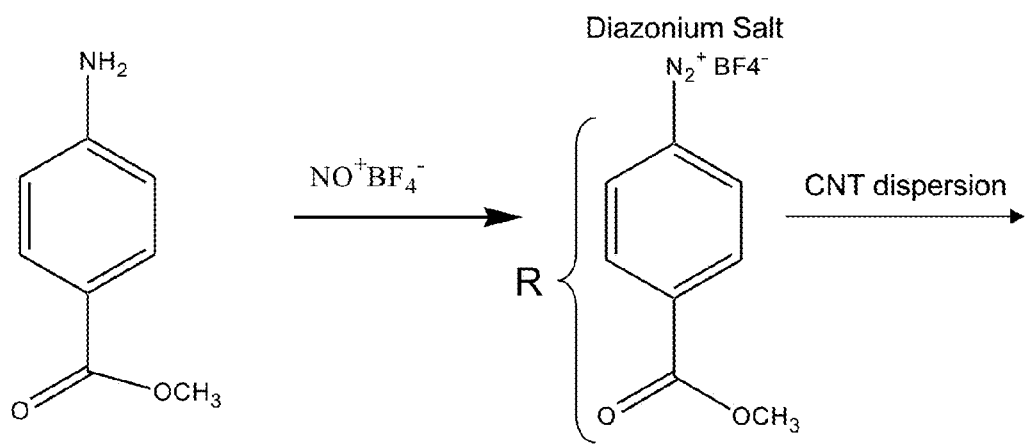
Fig. 8a
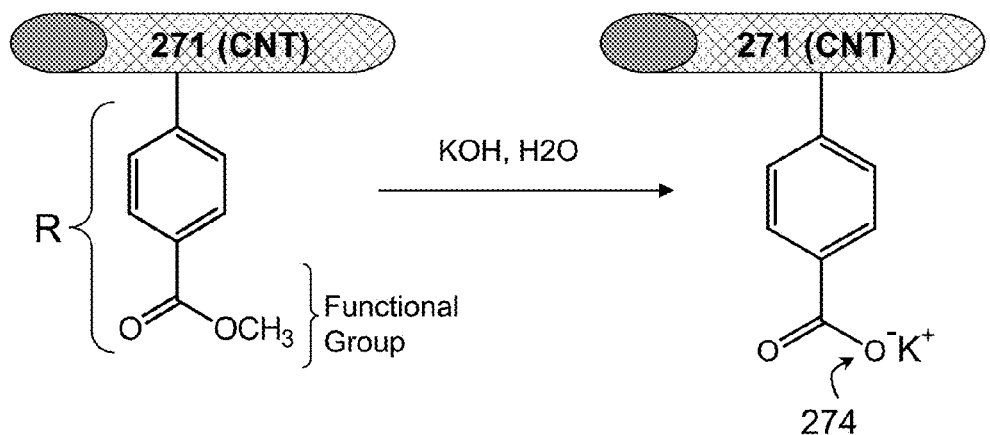
Fig. 8b
Fig. 8c

SELECTIVE PLACEMENT OF CARBON NANOTUBES VIA COULOMBIC ATTRACTION OF OPPOSITELY CHARGED CARBON NANOTUBES AND SELF-ASSEMBLED MONOLAYERS

PRIORITY

This application is a continuation of and claims priority from U.S. patent application Ser. No. 13/248,176, filed on Sep. 29, 2011, entitled "SELECTION PLACEMENT OF CARBON NANOTUBES VIA COULOMBIC ATTRACTION OF OPPOSITELY CHARGED CARBON ANNAOTUBES AND SELF-ASSEMBLED MONOLAYERS", the entire contents of which are incorporated herein by reference.

BACKGROUND

The present invention generally relates to a method of placing carbon nanotubes (herein after "CNTs") on a substrate. In particular, the invention relates to selective placement of charged CNTs on a pre-patterned surface having an oppositely charged, self-assembled monolayer.

CNTs can be semiconducting and therefore are of interest as channel materials for Field Effect Transistors (herein after "FET"). Accordingly, methods of placing CNTs on a substrate for use in FETs are being explored.

One approach to placing CNTs on a substrate involves directed assembly of CNTs from a suspension. In this approach, a substrate is patterned to define areas to which the CNT will have an affinity. The affinity is due to functionalization of either the substrate or the CNT to promote bonding between the substrate and the CNT.

In one instance, to place CNTs on a substrate, the prior art stamps a substrate with an organic compound to create a substrate having hydrophilic and hydrophobic regions. The hydrophilic region is the original substrate surface and the hydrophobic region is the area stamped with the organic compound. The substrate is immersed in a solution of CNTs and dried to leave CNTs on the hydrophilic regions. However, the CNTs on the surface of the substrate are bundled (i.e. a group of CNTs twisted together in a rope-like fashion) and/or multilayered. Bundled or multilayered CNTs are undesirable because a transistor made from them requires higher voltage to turn on an off. The described method has another drawback in that a solution of CNTs is not able to reach recessed hydrophilic areas having small widths (around or less than 200 nm). As a result, CNTs will be placed in large hydrophilic areas while small hydrophilic features remain uncovered. Accordingly, a CNT placement method based upon hydrogen bonding (a type of dipole bonding) can result in poor selectivity.

In other methods, the prior art places CNTs on a substrate by first functionalizing the CNT and then placing the CNT directly on the substrate. However, such methods result in a low density of CNTs on the surface.

Therefore, a need exists for a method of selectively placing a monolayer of high density CNTs on a substrate with minimal bundling.

SUMMARY

An object of the invention is to provide a method of forming a structure having selectively placed carbon nanotubes ("CNTs"). The method includes providing a substrate having a surface and contacting the surface of the substrate and a solution of a precursor molecule to form a self-assembled monolayer having a first ionic charge moiety on the surface. Thereafter, the self-assembled monolayer and a dispersion of a plurality of CNTs having a second ionic charge moiety are contacted.

According to another aspect of the invention a structure having a CNT layer includes a substrate having a first region and a second region, a self-assembled monolayer on the first region, and a CNT layer on the self-assembled monolayer. The CNT layer has a density exceeding 1 CNT per square micron.

According to a further aspect of the invention, a bi-functional precursor molecule for making self-assembled monolayers is disclosed. A bi-functional precursor molecule includes a first functional group to anchor the monolayer to a substrate and a second functional group having a first ionic charge moiety. The first functional group is selected from the following group: a thiol, an isontrile, a phosphonic acid and a hydroxamic acid. The first ionic charge moiety can be an onium salt including an ammonium salt, a sulfonium salt, and phosphonium salt.

Advantages of the present invention include increased density of nanotubes, and reduced formation of multilayer CNTs or bundled CNTs.

Another advantage is better electrical performance of a CNTFET.

Other characteristics and advantages of the invention will become obvious in combination with the description of accompanying drawings, wherein the same number represents the same or similar parts in all figures.

BRIEF DESCRIPTION OF THE DRAWINGS

FIG. 8a illustrates a first step in the method of forming a CNT having a second ionic charge moiety by functionalizing a CNT according to an embodiment of the invention, in the first step an organic salt is a diazonium salt (R—N2+X—) is combined with a CNT dispersion to form a functionalized CNT shown in FIG. 8b;

FIG. 8b illustrates a second step in a method of forming a CNT having a second ionic charge moiety by functionalizing a CNT according to an embodiment of the invention, in the second step KOH and water are mixed with the functionalized CNT to form the final product shown in FIG. 8c.

FIG. 8c illustrates the final product, the CNT having a second charge moiety, in a method of forming a CNT having a second ionic charge moiety by functionalizing a CNT according to an embodiment of the invention.

DETAILED DESCRIPTION

The basic principle of the invention is a method for forming a high density monolayer of CNTs on a substrate with little or no bundling. The method, as well as the resulting structure, will be described in conjunction with FIGS. 1-6. The invention also includes a bi-functional precursor molecule for self-assembled monolayers used in the method of placing the CNTs on a substrate. An embodiment of the bi-functional precursor is described in conjunction with FIG. 7. The invention further includes methods for creating CNTs having a second ionic charge moiety embodiments of which are described in conjunction with FIGS. 8-9. A detailed description of the invention is made in combination with the following embodiments. Please note that reference numbers are merely reference numbers and, thus, do not necessarily restrict the method to the numerical order of the reference numbers.

Figure 1:
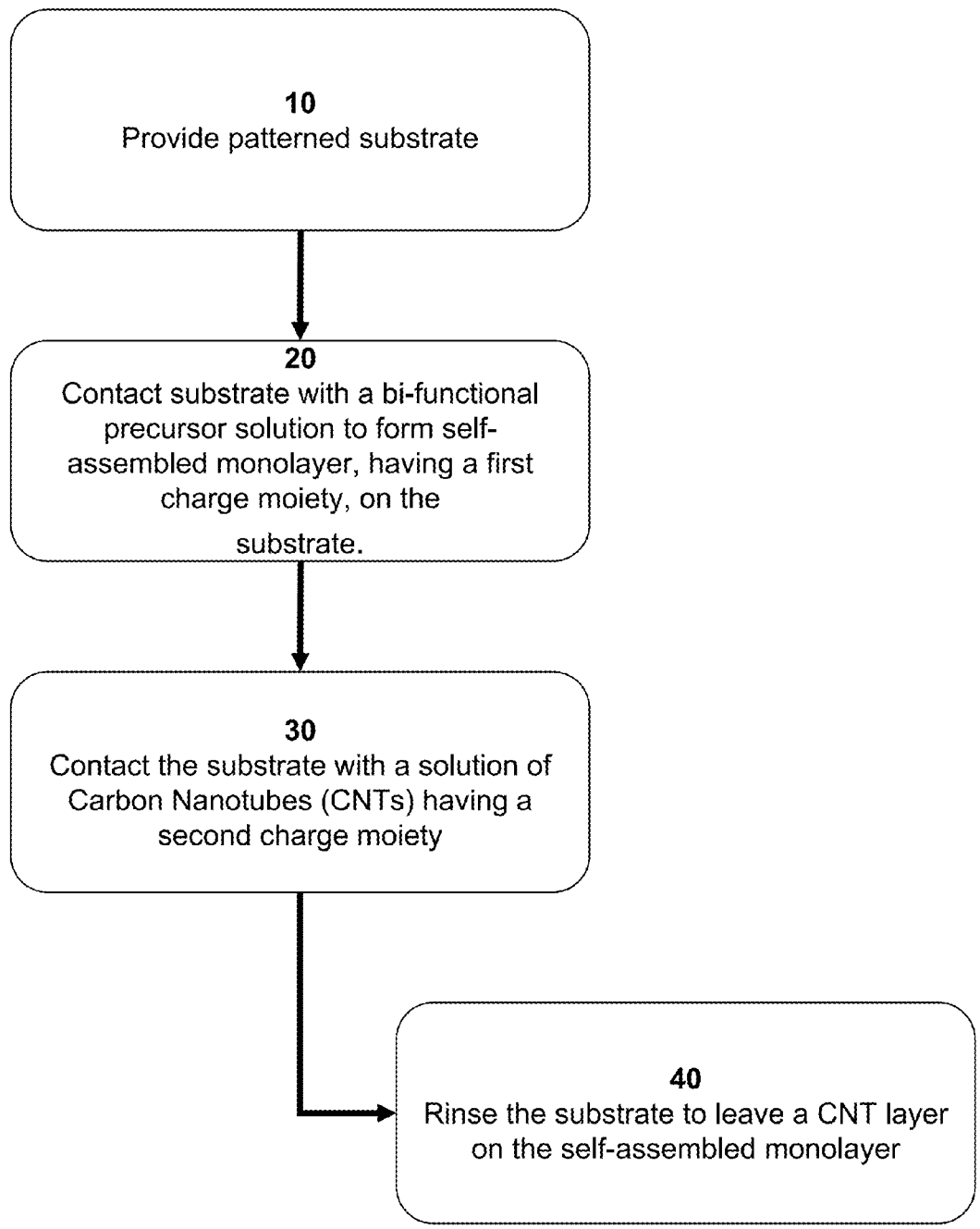
FIG. 1 is a flow chart of a method of placing CNTs above a substrate according to an embodiment of the invention.

Referring to FIG. 1, a flow chart of a method of placing CNTs above a substrate according to an embodiment of this invention is given. At reference numeral 10, a patterned substrate is provided. Patterning the substrate creates a first region and a second region on the substrate. At reference numeral 20, the patterned substrate is put in contact with a solution containing a precursor. The precursor is bi-functional, meaning it has two functional groups which serve two different purposes. The first functional group serves to anchor the precursor to the substrate and the second functional serves as (first) ionic charge moiety. By contacting the substrate to the precursor solution, the first functional group (the anchoring functional group) forms a bond with first region of the substrate thereby forming a self-assembled monolayer at that region; the second functional group remains in place, thus the monolayer has a first ionic charge moiety. At reference numeral 30, the substrate with self-assembled monolayer, is put in contact with a dispersion containing CNTs having a second ionic charge moiety. The first and second charge moieties are opposites, thus the CNTs are electrostatically attracted to the self-assembled monolayer having the first ionic charge moiety which results in a layer of CNTs on the self-assembled monolayer. At reference numeral 50, the substrate is rinsed to leave a CNT layer above the self-assembled monolayer, which in turn is above the first region of the substrate.

Figure 2A:
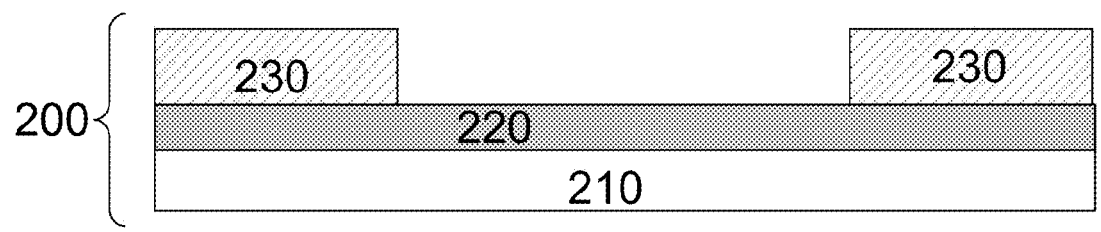
FIG. 2a illustrates a cross section of patterned substrate according to an embodiment of the invention.

Referring to FIG. 2a, a patterned substrate 200 is shown in cross-section. The substrate has a base 210, a first region 220 and a second region 230. Here, the second region 230 is shown as being higher than the first region 220, however, the regions could be co-planar or the first region 220 could be higher than the second 230. Here, the second region 230 is shown to be on top of a portion of the first region 220. However, the opposite formation could also occur, or the regions could abut each other. Thus, the exact cross-sectional configuration of the regions relative to each other and the base may have many varieties (even beyond those varieties discussed above), of which FIG. 2a is but one embodiment.

Figure 2B:
FIG. 2b illustrates a top down view of the patterned substrate of FIG. 2a according to an embodiment of the invention.

Referring to FIG. 2b, the same patterned substrate 200 is shown from a top-down perspective. In FIG. 2b the first region 220 is a simple strip that is flanked by the second regions 230. However, the first and second regions may take on a variety of shapes or configurations.

Next, isoelectric properties of the first and second regions are discussed. An isoelectric point is the pH at which a surface carries no net electric charge. In this invention, the first region 220 has a first isoelectric point and the second region 230 has a second isoelectric point. The first and second isoelectric points are different from each other, with the first isoelectric point (i.e. isoelectric point of the first region 220) being greater than the second isoelectric point (i.e. isoelectric point of the second region 230). Preferably, the difference of the isoelectric point of the first region and that of the second region should be about four or greater. For example, a first region 220 of hafnium oxide having an isoelectric point around 7 and a second region 230 of silicon dioxide having an isoelectric point around 2 results in a difference in the isoelectric points of about 5.

Next, materials suitable as first and second regions of the patterned substrate are discussed. In a first embodiment, the first region 220 is a metal oxide and the second region 230 is a non-metal oxide such as, but not limited to, a silicon oxide (SixOzHz). The metal oxide includes at least one metal from group IVB, VB, VIB, VIIB, VIII or IIA (CAS version) of the Periodic Table of the Elements. Illustratively, the metal oxide first region 220 can be an aluminum oxide (Al2O3), a hafnium oxide (HfO2), a titanium oxide (TiOx), or a zinc oxide (ZnO). In a second embodiment, the first region 220 can be any oxide, including non-metal oxides and metal oxides. In the second embodiment, the second region 230 is a metal. Examples of metals for use in the second region include gold, palladium, copper, platinum, etc.

Figure 3:
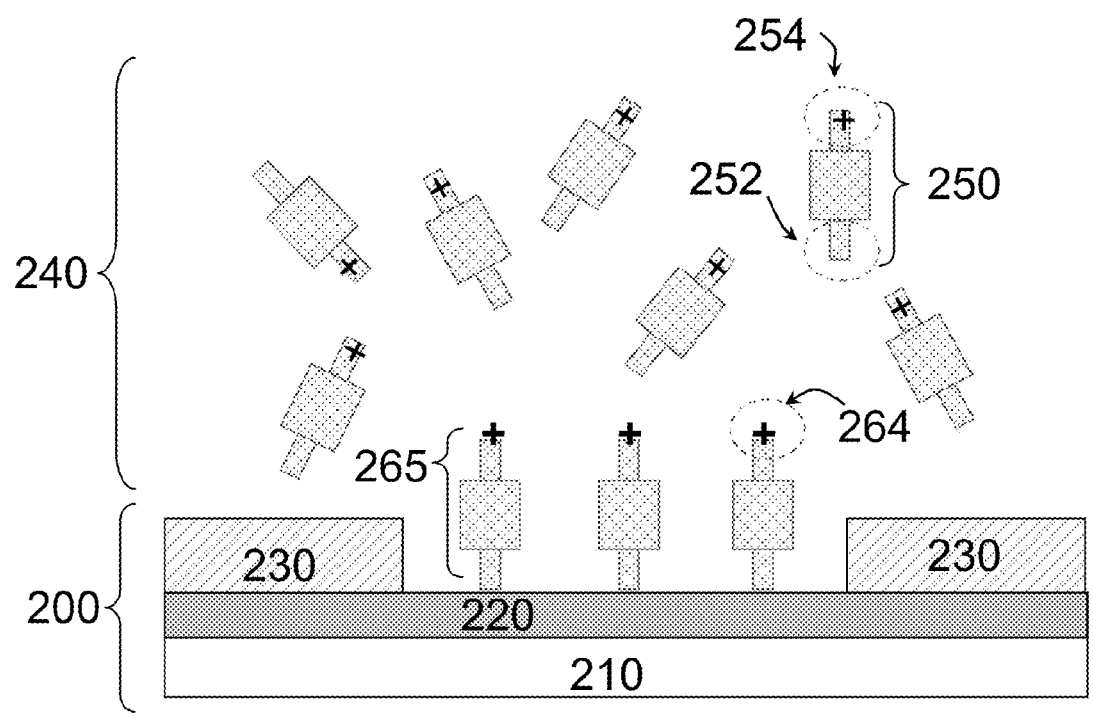
FIG. 3 illustrates bi-functional precursor material forming a self-assembled monolayer on regions of the substrate having a first isoelectric point according to an embodiment of the invention.

Referring to FIG. 3, the patterned substrate 200 comes in contact with a solution 240 containing a bi-functional precursor 250 to form a self-assembled monolayer (herein after "SAM") 265 having a first ionic charge moiety 264. The precursor 250 is bi-functional, meaning it has two functional groups (252, 254) which, in turn, serve two different purposes.

The first functional group 252 serves to anchor the precursor 250 to the first region 220 of the patterned substrate 200. The second functional group 254 has a first ionic charge moiety 264 which serves to form a bond with a second ionic charge moiety of the CNT later in the process. By contacting the patterned substrate 200 to precursor solution 240, the first functional group 252 (the anchoring functional group) forms a bond with first region 220 of the substrate thereby forming a self-assembled monolayer 265 having a first ionic charge moiety 264 at the first region 220. (Specific examples of bi-functional precursors and the first and second functional groups are discussed later).

The first ionic charge moiety 264 can be either positively or negatively charged. In a preferred embodiment, the patterned substrate 200 has a hafnium oxide first region 220 and a silicon oxide (SiOx) second region 230. In a preferred embodiment, the SAM 265 formed on the first region 220 (hafnium oxide) has a positive first ionic charge moiety 264. As a result, at that point in the particular preferred embodiment, the entire surface of the substrate is now hydrophilic prior CNT layer formation. This is in contrast to prior art methods relying on hydrophilicity and hydrophobicity differences on a substrate surface to determine selectivity of CNT placement. Thus, in the present invention, selectivity is, in part, determined by the isoelectric point difference in the first and second regions of the substrate.

Figure 4:
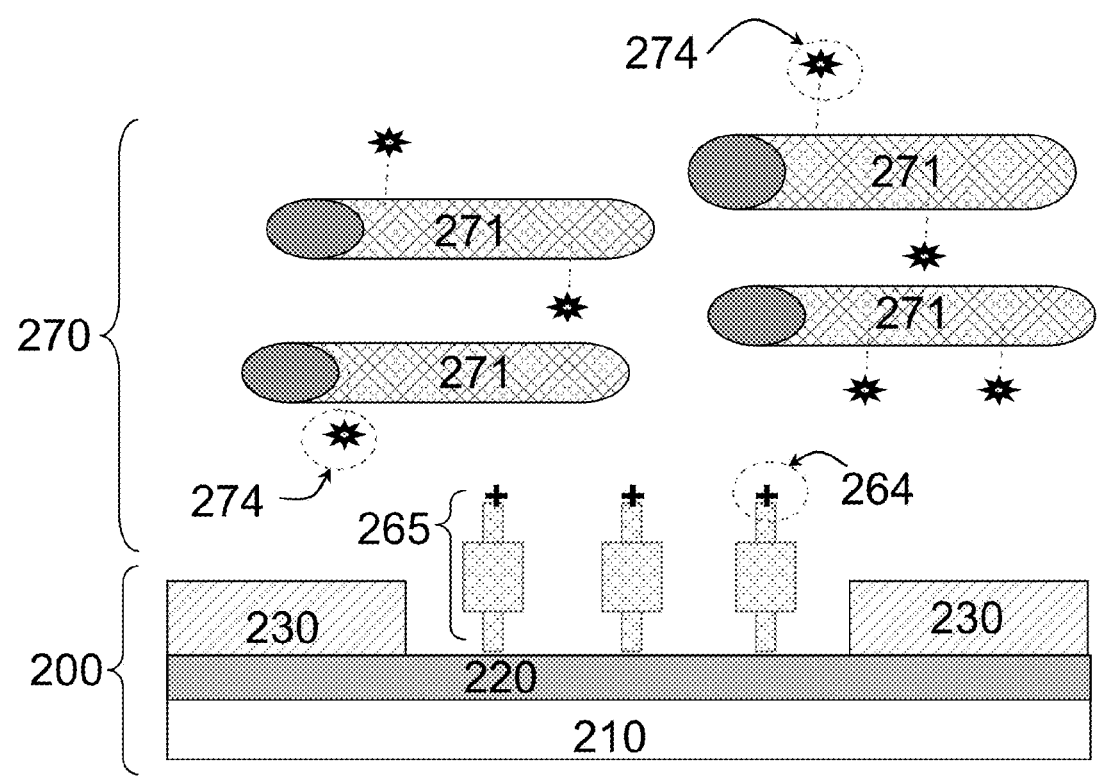
FIG. 4 illustrates a self-assembled monolayer with a first ionic charge moiety on the first region of the patterned substrate contacting a solution of CNTs having a second ionic charge moiety according to an embodiment of the invention.

Referring to FIG. 4, a SAM 265 with a first ionic charge moiety 264 on the first region 220 of the patterned substrate 200, contacts a solution 270 of CNTs 271 having a second ionic charge moiety 274. Ways of formation of the CNT having a second ionic charge moiety are discussed later. Coulombic attraction between the oppositely charged first ionic moiety 264 and second ionic moiety 274 bonds 284 the CNT 271 to the SAM 265 in the first region 220 of the substrate (See FIG. 5). The substrate is rinsed in water to form leave a CNT layer 290 selectively formed above the first region 220 of the patterned substrate 200. The rinsing step removes any excess CNTs to preferably form a monolayer of CNT. The CNTs of the layer 209 may be single walled or multi-walled CNTs. A rinsing step is possible in the present invention method because the bond 284 created between the oppositely charged ions of the CNTs and SAM is stronger than a mere hydrogen bond found in prior are methods. Thus, the bond 284 will not dissociate in water like a hydrogen bond can.

An advantage to the present invention that the charge moiety on the CNT is from a charged functionality or charged surfactant around the CNT, as opposed to an induced charge of the nanotube itself. By using a charged functionality or surfactant attached to the CNT, interaction between the CNT and the SAM covered substrate is increased which results in increased CNT density on the desired region of the substrate 200.

Figure 5:
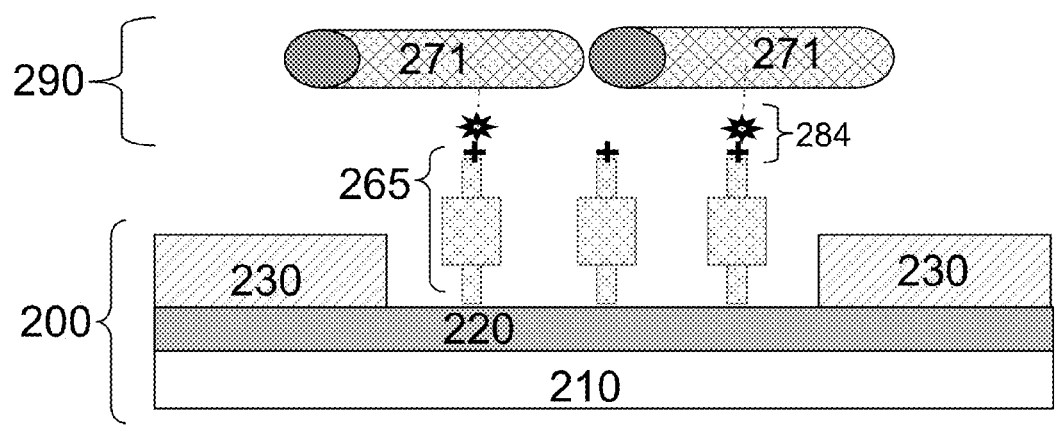
FIG. 5 illustrates a CNT layer on a self-assembled monolayer formed by a method according to an embodiment of the invention.
Figure 6:
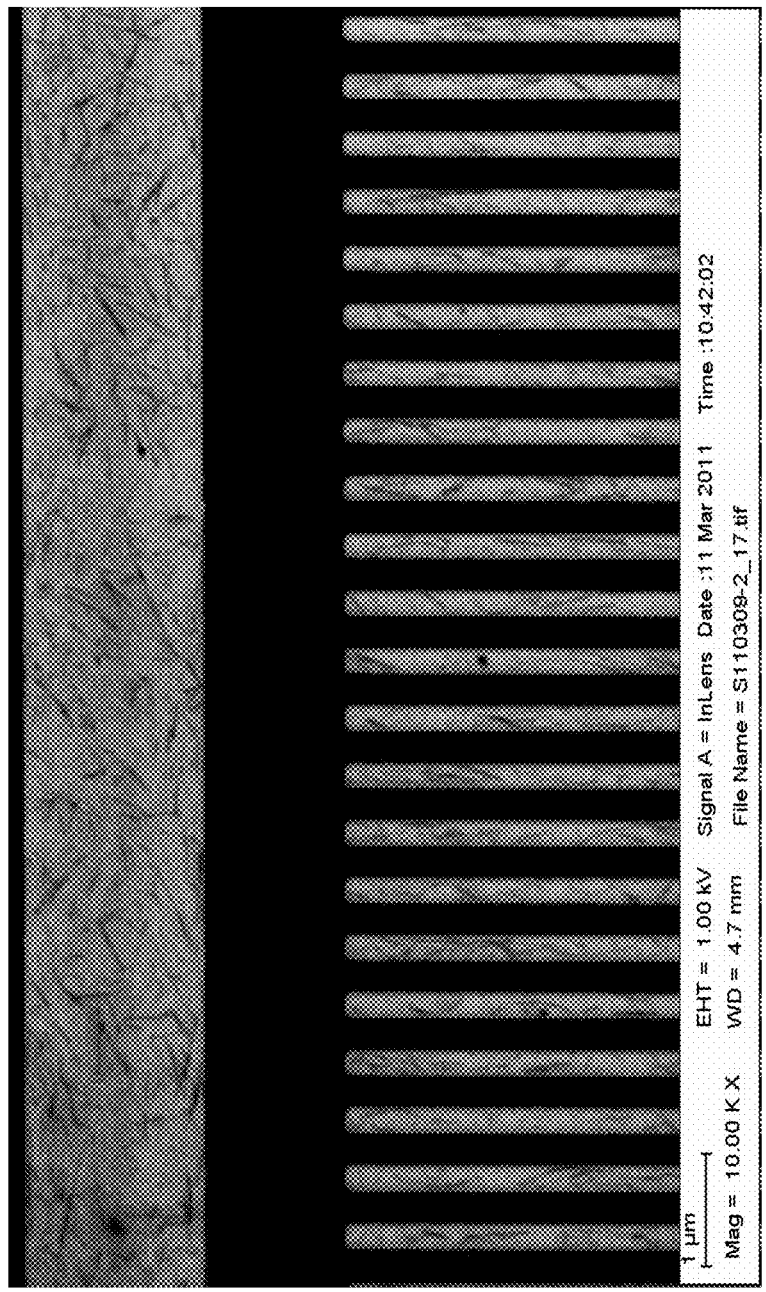
FIG. 6 is a scanning electron microscope image of substrate with a layer of selectively placed CNTs according to an embodiment of the invention.

Still referring to FIG. 5, the CNT layer 290 exhibits a density of CNTs from about 10 CNT/µm2 to about 100 CNT/µm2 and ranges therebetween. The resulting CNT layer 290 exhibits a reduced bundle density of from about 0.1 bundles/µm2 to about 1 bundles/µm2 and ranges therebetween. FIG. 6 is a scanning electron microscope image of substrate with selectively placed CNTs according to an embodiment of the invention.

Next, suitable bi-functional precursors 250 will be discussed. As stated earlier, the bi-functional precursor has a first functional group 252 for anchoring and a second functional group 254 for forming a first ionic charge moiety 264. The identity of the first functional group (the anchoring group) 252 depends upon the material of the first region 220. When the first region 220 material is a metal, the first functional group 252 is a thiol (—SH) or an isontrile (—NC). When the first region 220 material is a metal oxide, the first functional group 252 is a phosphonic acid (—PO3H2) or a hydroxamic acid (—CONHOH).

Next, the second functional group 254 of the bi-functional precursor 250 will be discussed. The second functional group 254 can be converted to the ionic charge moiety 264 (also referred to as charged ionic moiety in this application). The second functional group 254 can be converted to ionic charge moiety 264 either (1) before the precursor 250 anchors itself to the substrate to form a self-assembled monolayer, or (2) after the precursor 250 anchors itself to the substrate to form a self-assembled monolayer. In the first case, the self-assembled monolayer, as formed, has a first charge moiety 264. In the second case, initially the self-assembled monolayer is uncharged, and must be converted to a SAM having a first ionic charge.

Figure 7A:
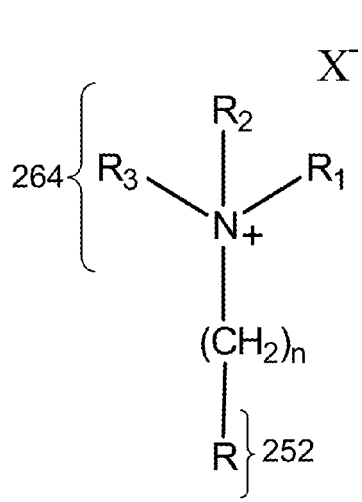
FIG. 7a illustrate a bi-functional precursor group having a first functional group and a second functional group which is an ammonium salt having a first ionic charge moiety according to an embodiment of the invention wherein the first ionic charge moiety is positively charged.
Figure 7B:
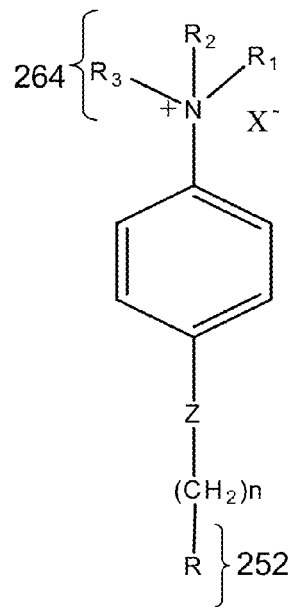
FIG. 7b illustrate a bi-functional precursor group having a first functional group and a second functional group which is an ammonium salt having a first ionic charge moiety according to an embodiment of the invention wherein the first ionic charge moiety is positively charged.
Figure 7C:
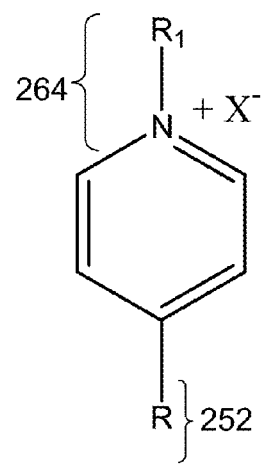
FIG. 7c illustrate a bi-functional precursor group having a first functional group and a second functional group which is a pyridinium salt having a first ionic charge moiety according to an embodiment of the invention wherein the first ionic charge moiety is positively charged.
Figure 7D:
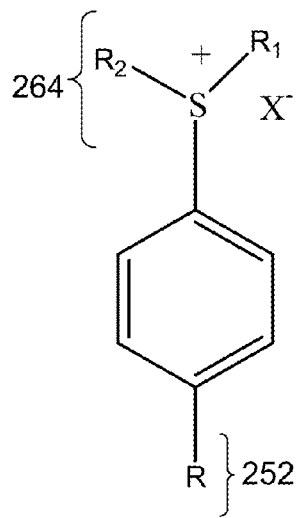
FIG. 7d illustrate a bi-functional precursor group having a first functional group and a second functional group which is a sulfonium salt having a first ionic charge moiety according to an embodiment of the invention wherein the first ionic charge moiety is positively charged.
Figure 7E:
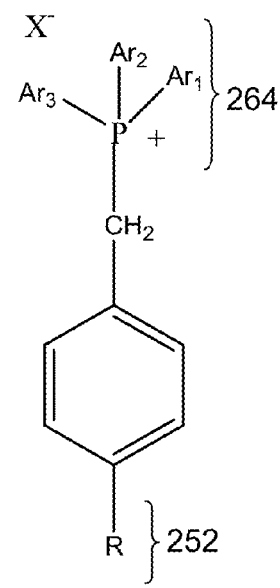
FIG. 7e illustrate a bi-functional precursor group having a first functional group and a second functional group which is a phosphonium salt having a first ionic charge moiety according to an embodiment of the invention wherein the first ionic charge moiety is positively charged.

Referring to FIGS. 7a-e, examples of bi-functional precursors 250 in which the second functional group 254 has been converted to a first ionic charge moiety 264 having a positive charged. All the bi-functional precursors 250 have an "R" group on the bottom which represents the first functional group 252 (i.e. the anchoring group) previously described. In FIGS. 7a-e, the first ionic charge moieties 264 are all positively charged onium salts. Specifically, FIGS. 7a-b illustrate ammonium salts, FIG. 7c is an example of pyridinium salt, FIG. 7d is a sulfonium salt, and FIG. 7e is a phosphonium salt. Continuing, in FIGS. 7a and 7b, "n" represents an integer from 2 to 16; in FIG. 7b "Z" represents a single bond, oxygen, NH or sulfur; in FIGS. 7a, 7b, 7c and 7d, "R1", "R2", and "R3" can independently be hydrogen, or an alkly group of one to ten carbons; in FIG. 7e "Ar1", "Ar2", and "Ar3" can independently be phenyl or substituted phenyl rings; and in all FIG. 7, "X" is a halogen. The ammonium salts pictured in FIGS. 7a-b are superior to a diazonium salt (—N2+) because a diazonium salt will form a covalent bond with a CNT (whether the CNT has a partial charge or full ionic charge). Covalent bonds degrade the electrical performance of a CNT in transistor and other electronic applications.

Second functional groups 254 that can be converted to positively charged moieties of FIG. 7 are as follows: ammoniums salts (FIGS. 7a and b) can be made by reacting an amine with acids; pyridinium salt (FIG. 7c) can be made by reacting pyridine with alkyl halides; sulfonium salt (FIG. 7d) can be made by reacting sulfides with alkyl halides; and phosphonium salt (FIG. 7e can be made by reacting triarylphosphines with alkyl halides.

While FIGS. 7a-e illustrate examples of a first ionic charge moiety 264 having a positive charge, a bi-functional precursor 250 having a negatively charged first ionic charge moiety 264 is also within the scope of the present invention. In the case of a negatively charged first ionic moiety, the bi-functional molecules are the same as FIGS. 7a-e with the exception that the positive charge moieties 264 are substituted with negative charged moieties such as —COO— or Ar—O—. Examples of second functional groups 254 that can be converted to negatively charged moieties 264 are carboxylic esters such as —COOCH3, and phenols. These groups are converted to the negatively charged moieties 264 by reacting with a strong base such as KOH to yield —COO— or Ar—O—, respectively.

Next, the term "ionic charge moiety" will be discussed. A moiety is a part of a molecule which has a charge. In the present invention, a charge is formed because one molecule takes an electron, or pair of electrons, from another; meaning the charge moiety is ionic. The ionically charged molecule of the present invention should be contrasted to a polar molecule (such as those found in water, —NH2, —NHNH2, —ONH2, —ONHOH, and —CONHO—). Polar molecules are molecules which have uneven electron distribution in a molecule. Because polar molecules have an uneven electron distribution, an atom in the molecule is sometimes referred to as partially charged or is said to have a dipole moment. However, the weak bonds which result from oppositely (partially) charged dipole-dipole attractions, should not be confused with the stronger bonds resulting from the attraction of oppositely charged ions of the present invention.

The discussion returns to the two ways of creating the second ionic charge moiety 274 on the CNTs 271. Functionalization, the first way of creating the second ionic charge moiety 274 on the CNT can be accomplished by mixing an aryl diazonium salt with a CNT dispersion to form a CNT covalently bonded to an organic compound having a functional group. The CNT with functional group is then placed in an aqueous strong base solution to convert the functional group to the second ionic charge moiety 274. Examples of strong bases include, but are not limited to, LiOH, NaOH, RbOH, CsOH, Ca(OH)2, Sr(OH)2, Ba(OH)2, and KOH, which is preferred.

Referring to FIGS. 8a-c, a specific example of functionalizing a CNT to form a negatively charged ionic moiety 274 is shown. In FIG. 8a, the organic salt is a diazonium salt (R—N2+X—) which is combined with a CNT 271 dispersion. Here, "R" of the diazonium salt is methyl benzoate. The salt bonds covalently with the CNT to form a CNT 271 having a functional group (i.e. a "functionalized CNT") in FIG. 8b. Continuing with FIG. 8b, KOH and water are mixed with the functionalized CNT to convert a portion of the functional group (here, the carboxylic ester —COOCH3) to the second ionic charge moiety 274 (here, —COO—).

A specific example of functionalizing a CNT to form a positively charged ionic moiety 274 is not shown in FIGS. 8a-c, however, a pyridine diazonium salt can be mixed with a CNT dispersion to form a functionalized CNT. Then the functionalized CNT is treated either with an acid to form pyridinium salt or with an alkyl halide (for example, but not limited to methyl iodide) to form N-alkylpyridinium halide. The treatments convert a portion of the functional group (here, pyridine) to the second ionic charge moiety 274 (here, CH3-X+).

Figure 9:
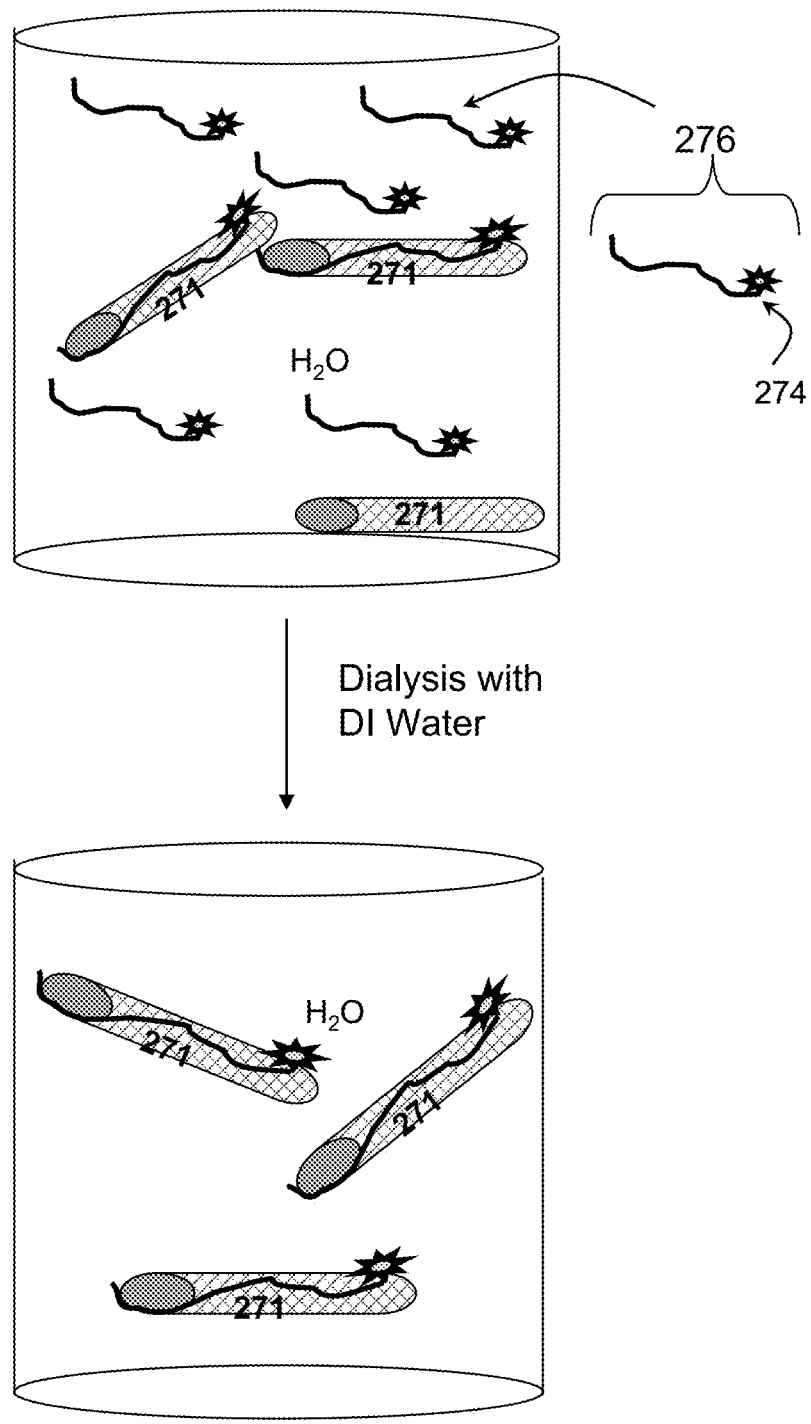
FIG. 9 illustrates a method of forming a CNT having a second ionic charge moiety by coating a CNT with an ionic surfactant according to an embodiment of the invention.

Referring to FIG. 9, coating, the second way of creating the second ionic charge moiety 274 is shown. Coating on the CNT can be accomplished by mixing CNTs 271 with a solution of an ionic surfactant 276 having the second charged ionic moiety 274. In FIG. 9, a water dispersion containing CNTs 271 is mixed with ionic surfactants 276. Some of the ionic surfactant 276 material forms a monolayer around the CNTs as shown in FIG. 9 as CNTs 271 with an overlapping ionic surfactant 276. The solution containing the CNT dispersion and ionic surfactant under goes dialysis in pure water to remove any excess ionic surfactant. By removing the excess ionic surfactant 276, the placement yield of the CNTs having a second ionic charge moiety on the SAM having a first ionic charge moiety increases because there is less likelihood that a SAM site will be occupied by an ionic surfactant 276 which is not associated with a CNT 271.

The second ionic charge moiety 274 will be oppositely charged from the first charged ionic moiety 264. Therefore, if the first ionic charge moiety 264 is positive, the ionic surfactant 276 will be anionic; if the first ionic charge moiety 264 is negative, the ionic surfactant 276 will be cationic. Examples of anionic surfactants include, but are not limited to DNA, sodium dodecyl sulfate and sodium cholate, in addition some lipids and phospholipids are useful as anionic surfactants. Examples of cationic surfactants include, but are not limited to, cetytlpyridinium chloride, diemthyldioctadecylammonium chloride.

The surfactants may be made ionic prior to coating the CNTs 271 or after coating the CNT 271. For example, the anionic surfactants can be prepared by treating their acid form with base and the cationic surfactants can be prepared by treating tertiary amines with alkyl halides.

An advantage of the present invention is that a bond 284 between a two charged molecules is stronger than a charge between a polar molecule and a CNT. Furthermore, the first ionic charge moieties 264 disclosed are superior to alternative moieties (for example, Ar—N2+) because the current first ionic charge moieties do not from covalent bonds with the CNT like Ar—N2+ does. In some cases, covalent bonds to a CNT may interfere with the electronic properties of the CNT. One electrical property of a CNT field effect transistor is its transfer characteristic (Id(A) vs. Vg(V)). A low ON current equates to poor performance and is an indicator of a covalent bond to the CNT. A higher ON current (10-7 A or more) indicates return of the lattice of the CNT and thus, no to minimal covalent bonding.

Next, example embodiments of the present invention are given.

Example I—Positively charged bi-functional precursor molecules for self-assembly. Potassium cyanide (50 mg) was added to a solution of methyl isonicotinate (1.17 g, 0.01 mole) and 50% hydroxylamine in water (1.3 g, 0.02 mole) in 10 mL tetrahydrofuran and 5 mL methanol. After stirring the mixture at room temperature for 18 hours, the precipitate was filtered and washed with diethyl ether and dried to give analytically pure N-hydroxy isonicotinamide. The latter was added to 5% methyl iodide in methanol and stirred at room temperature for two days. Methanol was evaporated under reduced pressure and the solid residue was crystallized from ethanol resulting in pure 4-hydroxamido-N-methylpyridinium iodide.

Example II—Preparation of negatively-charged CNTs by functionalization Nitrosonium tetrafluoroborate (12 mg, 1 mmole) was added to a suspension of methyl 4-aminobenzoate (15 mg, 1 mmole) in 5 mL of acetonitrile. The resulting solution was added drop-wise to an aqueous suspension of single-walled carbon nanotubes (1 mg) in water containing 1% sodium dodecylsulfate. After standing for 18 hours, the solution was centrifuged and the sediments were added to 10 mL of 10% methanolic potassium hydroxide solution. After stirring for 4 hours, 20 mL of acetone was added and the mixture centrifuged. The supernatant liquid was discarded and the sediment was dissolved in de-ionized water resulting in an aqueous solution of negatively charged carbon nanotubes.

Example III—Preparation of an aqueous dispersion of CNTs coating in with a monolayer of anionic surfactant. Dispersion of carbon nanotubes in 1% sodium dodecylsulfate was dialyzed with pure water for several days, during which fresh water was used after 24 hours. After several times dialyzing with fresh water, the solution inside the filter contains no free surfactant and all surfactants are attached to carbon nanotubes.

Example IV—Selective placement of carbon nanotubes. A silicon substrate patterned with silicon oxide regions and hafnium oxide regions was immersed in a 2 mM solution of 4-hydroxamido-N-methylpyridinium iodide in ethanol. After one hour, the substrate was removed from the solution and rinsed with copious amount of ethanol and dried under stream of nitrogen. The substrate, now coated with a positively charged ionic monolayer on the hafnium oxide, was then immersed in a solution of negatively charged (ionic, not dipole) functionalized nanotubes of example II. After one hour, the substrate was removed and washed thoroughly with de-ionized water and dried under stream of nitrogen. Scanning electron microscopy (FIG. 9) of the substrate showed selectively placed high density of carbon nanotubes on regions of hafnium oxide.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadcast interpretation so as to encompass all such modifications and equivalent structures and functions.

What is claimed is:

1. A structure having a self-assembled monolayer, comprising:
    a substrate having a surface;
    a precursor molecule forming a self-assembled monolayer, the precursor molecule having a first functional group to anchor the self-assembled monolayer to the surface of the substrate and a second functional group having a first ionic charge moiety on a surface of the self-assembled monolayer, the first functional group being selected from the group consisting of a thiol, an isontrile, a phosphonic acid and a hydroxamic acid and the first ionic charge moiety being an onium salt selected from the group consisting of an ammonium salt, a sulfonium salt, and phosphonium salt; and
    a plurality of carbon nanotubes (CNTs) having a second ionic charge moiety;
    wherein the first and second ionic charge moieties form a bond between the self-assembled monolayer and the plurality of carbon nanotubes (CNTs).

2. The structure of claim 1, wherein the first ionic charge moiety and the second ionic charge moiety are oppositely charged.

3. A structure having a self-assembled monolayer, comprising:
    a bi-functional precursor having a first functional group to anchor the self-assembled monolayer to a substrate, and a second functional group having a first ionic charge moiety;
    a carbon nanotube (CNT) layer arranged on the second functional group of the bi-functional precursor, the carbon nanotube layer comprising a second ionic charge moiety that bonds to the first charge moiety, and the carbon nanotube layer having a density that exceeds 1 carbon nanotube per square micron;
    wherein the first functional group is selected from the group consisting of a thiol, an isontrile, a phosphonic acid and a hydroxamic acid, and the first ionic charge moiety is an onium salt selected from the group consisting of an ammonium salt, a sulfonium salt, and phosphonium salt.

* * * * *